United States Patent
Pischl et al.

(10) Patent No.: US 10,265,108 B2
(45) Date of Patent: Apr. 23, 2019

(54) BONE PLATE

(75) Inventors: Susanne Pischl, Voehringen (DE); Steffen Dirr, Voehringen (DE)

(73) Assignee: ULRICH GMBH & CO. KG, Ulm (DE)

( * ) Notice: Subject to any disclaimer, the term of this patent is extended or adjusted under 35 U.S.C. 154(b) by 159 days.

(21) Appl. No.: 13/293,375

(22) Filed: Nov. 10, 2011

(65) Prior Publication Data

US 2013/0023939 A1    Jan. 24, 2013

(30) Foreign Application Priority Data

Jul. 20, 2011 (DE) .......................... 10 2011 051 975

(51) Int. Cl.
*A61B 17/80* (2006.01)
*A61B 17/70* (2006.01)

(52) U.S. Cl.
CPC ...... *A61B 17/8047* (2013.01); *A61B 17/7049* (2013.01); *A61B 17/7052* (2013.01); *A61B 17/7055* (2013.01); *A61B 17/8061* (2013.01)

(58) Field of Classification Search
CPC . A61B 17/8047; A61B 17/8033; A61B 17/80; A61B 17/8061; A61B 17/8605; A61B 17/862; A61B 17/8695; A61B 17/70; A61B 17/7055; A61B 17/7044; A61B 17/7049; A61B 17/7052; A61B 17/7058; A61B 17/7059; A61B 17/8023
USPC ...... 606/70–71, 280–299; 411/353, 517, 999
See application file for complete search history.

(56) References Cited

U.S. PATENT DOCUMENTS

| | | | | |
|---|---|---|---|---|
| 895,842 | A * | 8/1908 | Chambers, Jr. ................ | 411/213 |
| 4,367,602 | A * | 1/1983 | Petersen .......................... | 37/459 |
| 6,607,149 | B2 * | 8/2003 | Smith et al. ................ | 239/585.1 |
| 7,001,389 | B1 * | 2/2006 | Navarro et al. ................. | 606/71 |
| 2005/0049593 | A1 * | 3/2005 | Duong ............... | A61B 17/8047 606/287 |
| 2005/0240185 | A1 * | 10/2005 | Boomer ............. | A61B 17/7055 606/277 |
| 2006/0155285 | A1 | 7/2006 | Anderson | |
| 2006/0241616 | A1 * | 10/2006 | Konieczynski et al. ........ | 606/69 |
| 2007/0043369 | A1 * | 2/2007 | Wallenstein et al. ........... | 606/69 |
| 2012/0065690 | A1 * | 3/2012 | Perrow .............. | A61B 17/7059 606/294 |

* cited by examiner

Primary Examiner — Eric S Gibson
Assistant Examiner — Marcela I Shirsat
(74) *Attorney, Agent, or Firm* — Andrew Wilford

(57) ABSTRACT

A bone plate is formed with a throughgoing hole formed with a radially inwardly open outer groove. A screw fastener has a shaft engageable coaxially through the hole and a head of larger diameter than the shaft and adapted to bear axially on the plate around the hole. The shaft is formed offset from the head with a radially outwardly projecting ridge defining a radially outwardly open inner groove aligned radially with the outer groove when the fastener is fitted through the hole with the head bearing on the plate. An elastically deformable ring of a diameter generally equal to that of the hole at the outer groove is formed with at least one radially inwardly directed projection that, when the ring is fitted to the outer groove and the fastener is seated in the hole, projects radially inward into the inner groove of the fastener.

11 Claims, 3 Drawing Sheets

BONE PLATE

FIELD OF THE INVENTION

The present invention relates to a bone plate. More particularly this invention concerns a bone-plate assembly, in particularly an occipital bone plate.

BACKGROUND OF THE INVENTION

An orthopedic implant, in particular, a bone plate, preferably an occipital plate such as describes in US 2006/0155285, comprises at least one throughgoing hole for a fastener anchorable in a bone and having a shaft and a head. A groove is formed in the throughgoing hole and guiding a flexible ring.

The flexible ring protects the fastener from disengaging from the bone and thus from the bone plate. In order to be able to then remove the fastener from the bone, cylindrical holes are provided on the edges of the throughgoing hole that provide access for a tool that can expand the flexible ring. Fabrication of this bone plate is very expensive, added to which is the fact that an unnecessary number of tools is employed to anchor the fastener in the bone material or to then disengage them.

OBJECTS OF THE INVENTION

It is therefore an object of the present invention to provide an improved bone plate.

Another object is the provision of such an improved bone plate that overcomes the above-given disadvantages, in particular that by simple means provides the desired anchoring and disengagement of the fastener from the bone and from the bone plate, where any unwanted disengagement is prevented.

SUMMARY OF THE INVENTION

A bone plate is formed with a throughgoing hole centered on an axis and formed with a radially inwardly open outer groove. A screw fastener has a shaft engageable coaxially through the hole and a head of larger diameter than the shaft and adapted to bear axially on the plate around the hole. The shaft is formed offset from the head with a radially outwardly projecting ridge defining a radially outwardly open inner groove aligned radially with the outer groove when the fastener is fitted through the hole with the head bearing on the plate. An elastically deformable ring of a diameter generally equal to that of the hole at the outer groove is formed with at least one radially inwardly directed projection that, when the ring is fitted to the outer groove and the fastener is seated in the hole, projects radially inward into the inner groove of the fastener.

This is associated with the advantage that the circumferential ridge interacts with the projection of the flexible ring when the fastener is screwed in or unscrewed, thereby ensuring secure seating of the fastener within the bone plate. This prevents any unintended disengagement of the fastener due to the shaft's being clamped by the projection.

It is especially advantageous if the projection is formed by an indentation or bends in the flexible ring, which is of uniform cross-sectional size and shape. As a result, the flexible ring can be produced very cost-efficiently as a molded part. If two indentations are provided, the flexible ring can be inserted quite easily into the groove since the ring can now be compressed using forceps.

In order to also ensure secure central seating of the flexible ring in the plate, it is especially advantageous when the diameter of the flexible ring and of the groove are such as to enable the flexible ring to retract into the groove in a rest position, only projecting from it at the projections that can also be pushed back into the outer groove, for instance when the screw is forced through the hole.

It is furthermore advantageous for the flexible ring to have a gap. This aspect allows the ring to be more easily inserted into the groove of the throughgoing hole by elastic deformation.

It has proven especially advantageous if the flexible ring has at least one, preferably exactly two, straight portions. These straight portions enable a relatively greater pressure to be exerted on the shaft to be clamped. In particular, an approach has proven successful for clamping the shaft whereby the projection, which is preferably formed as an indentation, is provided on the straight portion.

It is furthermore advantageous for the elastic deformation of the flexible ring if the gap is on a semicircular side of the flexible ring, between the straight portions.

Within the scope of the invention, the preferred approach is for the ridge to taper radially outward, that is have a flank turned away from the head that forms an acute angle with the screw/hole axis. The tapered ridge enables the flexible ring to expand during the intentional screwing-in or unscrewing of the fastener. Its opposite flank, the one turned toward the head, can be more perpendicular to prevent the screw fastener from backing out and pushing the ring into the outer groove. Thus the pitch of flanks of the ridge is smaller on the outer flank turned away from the head than on its opposite inner flank. As a result, the outer flank is shallower than the inner flank. This ensures that the fastener can be easily screwed into the bone, where the distal contact bevel functions to expand the flexible ring without having to apply a large force against the spring tension of the clamping flexible ring. Due to the steep proximal contact bevel, a large force must be applied against the spring tension of the flexible ring to again disengage the fastener from the bone plate.

It has proven advantageous here if the inner shaft groove is formed between the head and the ridge. This enables the flexible ring even more effectively to clamp the fastener, or to secure it by positive-fitting engagement.

If the throughgoing hole has a countersink, the fastener can then also be screwed into the bone material at an angle relative to the horizontal plane of the bone plate. In addition, the head can be seated flush with the outer surface of the implant in the throughgoing hole.

BRIEF DESCRIPTION OF THE DRAWING

The above and other objects, features, and advantages will become more readily apparent from the following description, reference being made to the accompanying drawing in which.

DETAILED DESCRIPTION

Figure 1:
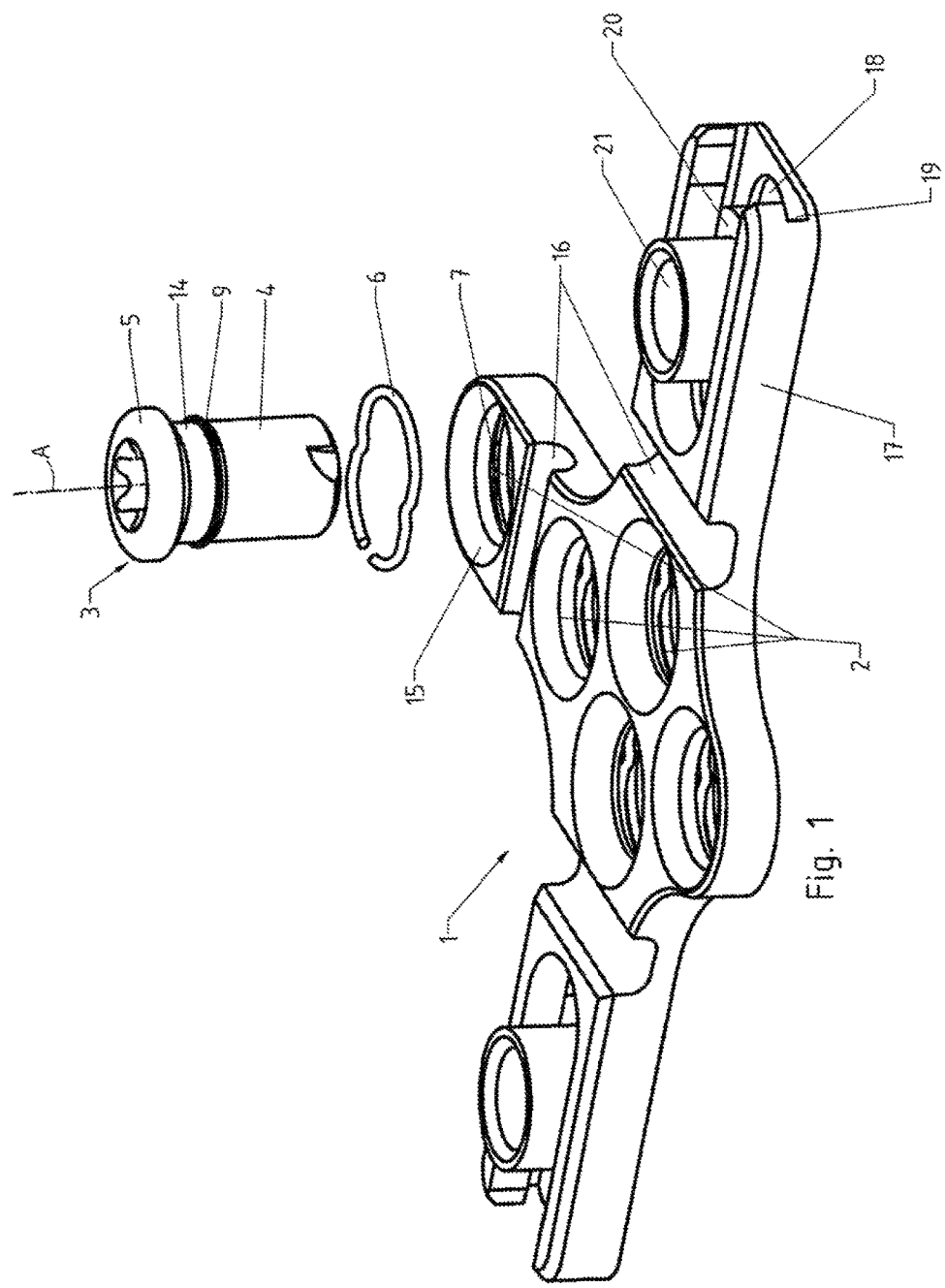
FIG. 1 is an exploded perspective view of the bone plate according to the invention.
Figure 2:
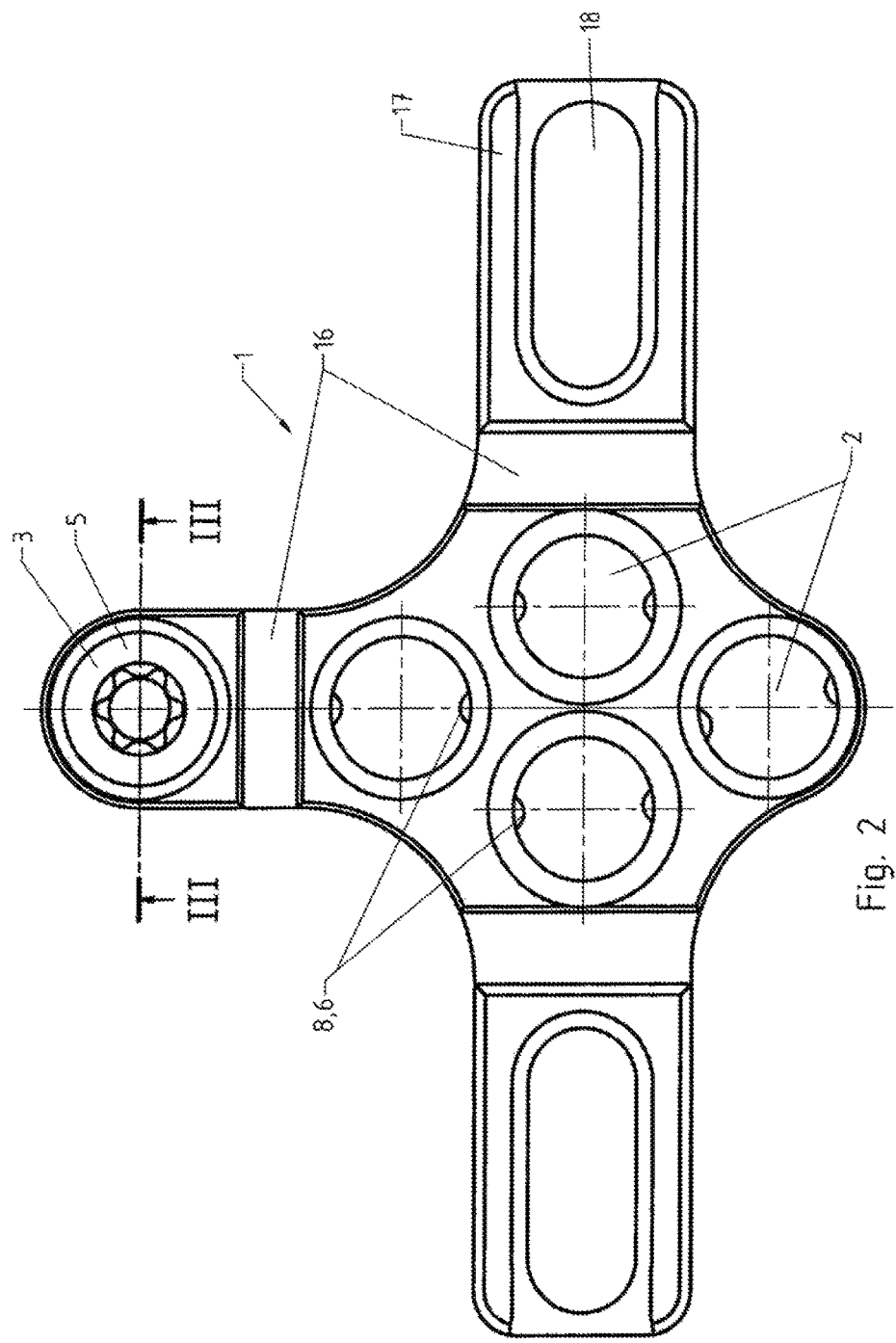
FIG. 2 is a top view of the bone plate.

As seen in FIGS. 1 and 2 an implantable bone plate 1, specifically an occipital plate, is formed with at least one throughgoing hole 2 for a screw fastener 3 anchorable in unillustrated bone. The fastener 3 has a shaft 4 and a head 5 and the plate 1 is formed inside the hole 2 with, relative to a central axis A, a radially inwardly open groove 7 holding a flexible elastic snap ring 6. This ring 6 has at least one radially inward projection 8 that serves to axially lock the plate 1 to the screw's shaft 4.

A circumferential radially outwardly projecting ridge 9 formed on the shaft 4 below the head 5 forms with the head 5 a radially outwardly open groove 14 into which the projections 8 extend. In the illustrated embodiment, the bone plate 1 has five throughgoing holes 2 for fasteners 3 that can be bone screws having a screw thread 24 (FIG. 3) extending completely or partially along shaft 4, or of another type of fastener such as, for example an unthreaded nail.

Figure 4:
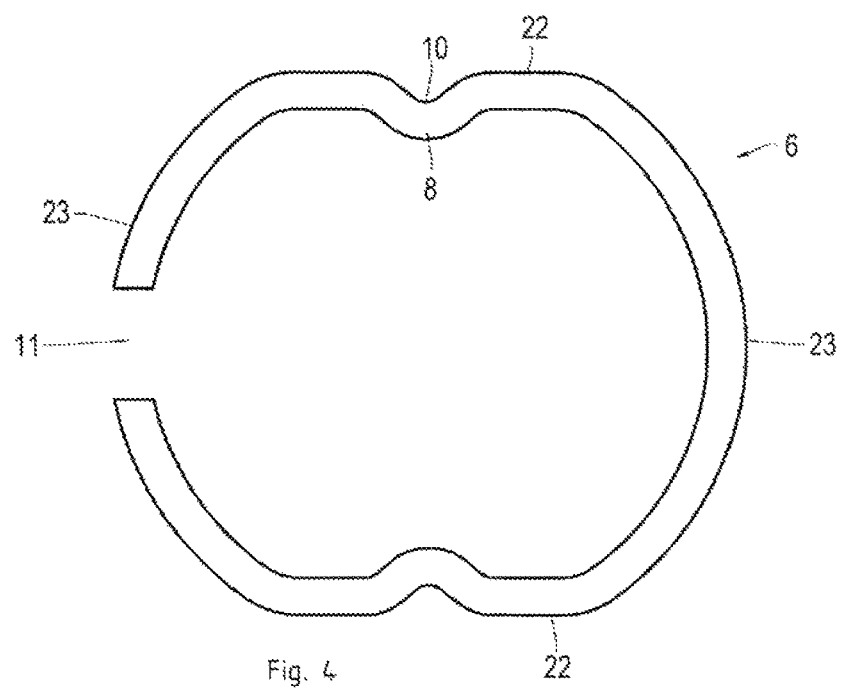
FIG. 4 is a large-scale top view of the retaining ring according to the invention.

As FIG. 4 shows, each projection 8 is formed by an indentation 10 in the flexible ring 8, which is of uniform circular cross section and size. In addition, the diameter of flexible ring 6 is smaller than the radial depth of the groove 7 so as to allow the ring 6 to retract into groove 7, with only the projections projecting out of the groove 7 into the hole 2. The flexible ring 6 is annularly discontinuous and has a gap 11 and two straight portions 22 on which the diametrally opposite indentations 10 are provided. The gap 11 is on one of two semicircular sides 23 of the ring 6, each of which is formed centrally with the respective straight portion, so that the ring 6 is symmetrical to a plane bisecting the gap 11 and parallel to the straight portions 22. These semicircular sides 23 here can bear radially outwardly on the floor of the groove 7 to ensure central seating of the ring 6.

The bone plate 1 in this embodiment has three bending zones 16 so as to enable it to be optimally fitted to the bone. In addition, two plate wings 17 are provided onto which one rod each can be installed that can rigidly attach the plate wings to the underlying vertebrae, as is generally provided with such bone plates to stabilize the spinal column.

Each plate wing 17 has a respective elongated hole or slot 18 and a respective guide track 19 for a guide element 20 to which the above-mentioned rod can be attached. Each guide element 20 has a threaded collar 21.

Figure 3:
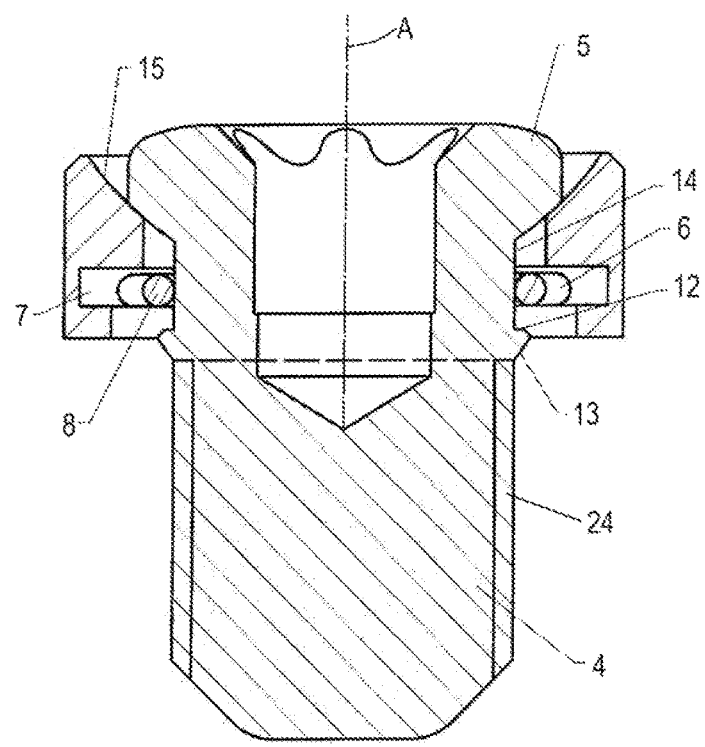
FIG. 3 is a large-scale vertical section taken along line III-III of FIG. 2.

As shown in FIG. 3 the ridge 9 is basically sawtooth-shaped, with a flank 12 turned toward the head 5 that is at least partially generally perpendicular to the axis A and an opposite flank 13 turned away from the head 5 that is of a more gentle acute angle, here around 45°. The throughgoing hole 2 has a countersink bevel 15.

In addition the underside of the head 5 is generally frustoconical, and even rounded somewhat so as to be complementary to the bevel 15. The shank 4 is of substantially smaller diameter than the hole 2 so that the screw 3 does not have to be in perfect coaxial alignment with the hole 2. Nor do the axes of the screw 6 and hole 2 have to be exactly coaxial, but can extend at a small acute angle to each other, as conditions demand.

We claim:

1. An orthopedic implant comprising:
   an occipital bone plate formed with a throughgoing hole centered on an axis and formed with a radially inwardly open and annular outer groove of a predetermined axial width;
   a wing extending radially from the plate and formed with a hole for attachment of a rod of an orthopedic implant;
   a bending zone attaching the wing to the plate and permitting the wing to deflect relative to the plate;
   a bone screw having a shaft engageable coaxially through the hole and a head of larger diameter than the shaft and adapted to bear axially on the plate around the hole, the shaft being formed offset from the head with a radially outwardly projecting annular ridge defining a radially outwardly open inner groove of an axial width greater than the predetermined axial width of the outer groove and aligned radially with the outer groove when the screw is fitted through the hole with the head bearing on the plate; and
   an elastically deformable ring in the outer groove and having, in a rest position, an inside diameter corresponding to that of the hole at the outer groove, annularly surrounding the shaft, and formed with two radially inwardly directed projections that in the rest position of the ring when the ring is fitted to the outer groove and the screw is seated in the hole, project radially inward from the outer groove into the inner groove of the screw to axially couple the screw to the plate while permitting limited relative axial movement of the ring in the inner groove, the outer groove being of a radial depth such that the projections can be radially elastically pressed back to a position wholly recessed in the outer groove.

2. The orthopedic implant defined in claim 1, wherein the ring is of uniform cross-sectional shape and size and the projection is formed by bends in the ring.

3. The orthopedic implant defined in claim 1, wherein the ring is dimensioned such that in the rest position all of the ring except the projections is recessed in the outer groove.

4. The orthopedic implant defined in claim 1, wherein the ring is annularly discontinuous.

5. The orthopedic implant defined in claim 4, wherein the ring has a pair of straight portions.

6. The orthopedic implant defined in claim 5, wherein the ring is formed with a gap equidistant between the straight portions.

7. The orthopedic implant defined in claim 1, wherein the ridge has a flank forming with the axis an acute angle.

8. The orthopedic implant defined in claim 7, wherein the flank forming the acute angle with the axis is directed away from the head of the screw and the ridge has a flank turned toward the head and extending perpendicular to the axis.

9. The orthopedic implant defined in claim 1, wherein the plate is formed around the hole with an annular recess in which the head sits when the screw is fitted to the hole.

10. The orthopedic implant defined in claim 9, wherein the recess has a frustoconical surface and the head has a complementary surface engageable therewith.

11. The orthopedic implant defined in claim 1, wherein the ring is made of a wire having a diameter equal to the predetermined axial width of the outer groove such that the ring is axially nonmovable in the plate.

* * * * *